(12) United States Patent
Coffin

(10) Patent No.: US 7,063,851 B2
(45) Date of Patent: *Jun. 20, 2006

(54) HERPES VIRUSES FOR IMMUNE MODULATION

(75) Inventor: Robert S. Coffin, London (GB)

(73) Assignee: Biovex Limited, London (GB)

(*) Notice: Subject to any disclaimer, the term of this patent is extended or adjusted under 35 U.S.C. 154(b) by 390 days.

This patent is subject to a terminal disclaimer.

(21) Appl. No.: 10/273,348

(22) Filed: Oct. 18, 2002

(65) Prior Publication Data

US 2004/0022812 A1 Feb. 5, 2004

Related U.S. Application Data

(63) Continuation-in-part of application No. 09/833,073, filed on Apr. 12, 2001, now Pat. No. 6,713,067.

(30) Foreign Application Priority Data

Apr. 12, 2000 (GB) .................................. 0009079

(51) Int. Cl.
A61K 39/245 (2006.01)
A61K 35/26 (2006.01)
A61K 39/294 (2006.01)
A61K 48/00 (2006.01)
C12N 5/10 (2006.01)

(52) U.S. Cl. ............................... 424/199.1; 424/229.1; 424/230.1; 424/231.1; 424/93.2; 424/93.21; 424/278.1; 424/205.1; 435/355; 435/372; 435/325; 435/235.1; 435/320.1

(58) Field of Classification Search .. 424/229.1–231.1, 424/93.2, 93.21, 278.1, 199.1, 205.1; 435/235.1, 435/320.1, 325, 355, 372
See application file for complete search history.

(56) References Cited

U.S. PATENT DOCUMENTS 6,713,067 B1 * 3/2004 Coffin ...................... 424/199.1
2004/0219167 A1 * 11/2004 Coffin ...................... 424/199.1

FOREIGN PATENT DOCUMENTS

| WO | WO 94/03207 | 2/1994 |
| WO | WO 97/13866 | 4/1997 |
| WO | WO 98/04726 | 2/1998 |
| WO | WO 98/30707 | 7/1998 |
| WO | WO 98/51809 | 11/1998 |
| WO | WO-98/51809 | * 11/1998 |
| WO | WO 99/60145 | 11/1999 |
| WO | WO-00/08191 | * 2/2000 |
| WO | WO 00/08191 | 2/2000 |
| WO | WO 00/08891 | 2/2000 |
| WO | WO 01/77358 | 10/2001 |

OTHER PUBLICATIONS

Krisky et al Gene Therapy 5:1517-1530, 1998.*

Walker et al, Vaccine 16(1):1-5 (1998).
Walker et al, "Postexposure vaccination with a virion host shutoff defective mutant reduces UV-B radiation-induced ocular herpes simplex virus shedding in mice", Vaccine 16(1):6-8 (1998).
Strelow et al, "Role of the Virion Host Shutoff (vhs) of Herpes Simplex Vi9rus Type 1 in Latency and Pathogenesis", Journal of Viroloty 69:6779-6786 (1995).
Geiss et al, "Disruption of Virion Host Shutoff Activity Improves the Immunogenicity and Protective Capacity of a Replication-Incompetent Herpes Simplex Virus Type 1 Vaccine Strain", Journal of Virology 74(23):111137-11144 (2000).
Huard et al, "Gene transfer to muscle using herpes simplex virus-based vectors", Neuromuscular Disorders 7(5):299-313 (1997)—Abstract.
Coffin et al, "Pure populations of transduced primary human cells can be produced using GFP expressing herpes virus vectors and flow cytometry" Gene Therapy 5:718-722 (1998).
Coffin et al, "Gene delivery to the central and peripheral nervous systems of mice using HSV1 ICP34.5 deletion mutant vectors" Gene Therapy 3:886-891 (1996).
Walker et al, Vaccine 16:1-5 (1998).
Walker et al, "Postexposure vaccination with a virion host shutoff defective mutant reduces UV-B radiation-induced ocular herpes simplex virus shedding in mice" Vaccine 16:6-8 (1998).
Strelow et al, Role of the virion host shutoff (vhs) of herpes simplex virus type 1 in latency and pathogenesis J. of Virology 69:6779-6786 (1995).
Geiss et al, "Disruption of virion host shutoff activity improves the immunogenicity and protective capacity of: replication-incompetent herpes simplex virus type 1 vaccine strain" J. of Virology 74:11137-11144 (2000).
Huard et al, "Gene transfer to muscle using herpes simplex virus-based vectors" Neuromuscular Disorders 7:299-313 (1997)—Abstract only.

(Continued)

Primary Examiner—Mary E. Mosher
(74) Attorney, Agent, or Firm—Nixon & Vanderhye P.C.

(57) ABSTRACT

A method of stimulating an immune response in a human or animal subject, which method comprises administering to a subject in need thereof an effective amount of an attenuated herpes virus which:

(i) lacks a functional vhs gene, or a functional equivalent thereof;
(ii) lacks a functional ICP47 gene, or a functional equivalent thereof; and
(iii) is incapable of expressing a substantial amount of functional ICP22, or a functional equivalent thereof, in mammalian dendritic cells.

36 Claims, No Drawings

OTHER PUBLICATIONS

MacLean et al, "Herpes simplex virus type 1 deletion variants 1714 and 1716 pinpoint neurovirulence-related sequences in Glasgow strain 17+ between immediate early gene 1 and the 'a' sequence" J. Gen. Virology 72:631-639 (1991).

Chou et al, "Differential response of human cells to deletions and stop codons in the $_{\gamma 1}$34.5 gene of herpes simplex virus" J. Virology 68:8304-8311 (1994).

Chou & Roizman, "The $_{\gamma 1}$34.5 gene of herpes simplex virus 1 precludes neuroblastoma cells from triggering total shutoff of protein synthesis characteristic of programmed cell death in neuronal cells" Proc. Natl. Acad. Sci. USA 89:3266-3270 (1992).

Gendler et al, "Molecular cloning and expression of human tumor-associated polymorphic epithelial mucin" J. Biol. Chem. 265:15286-15293 (1990).

Aicher et al, "Successful retroviral mediated transduction of a reporter gene in human dendritic cells: Feasibility of therapy with gene-modified antigen presenting cells" Exp. Hematology 25:39-44 (1997).

Samaniego et al, "Functional interactions between herpes simplex virus immediate-early proteins during infection: Gene expression as a consequence of ICP27 and different domains of ICP4" J. Virology 69:5705-5715 (1995).

Zitvogel et al, "Therapy of murine tumors with tumor peptide-pulsed dendritic cells: dependence on T cells, B7 costimulation, and T helper cell 1-associated cytokines" J. Exp. Med. 183:87-97 (1996).

Celluzzi et al, "Peptide-pulsed dendritic cells induce antigen-specific, CTL-mediated protective tumor immunity" J. Exp. Med. 183:283-297 (1996).

Reeves et al, "Retroviral transduction of human dendritic cells with a tumor-associated antigen gene" Cancer Research 56:5672-5677 (1996).

Arthur et al, "A comparison of gene transfer methods in human dendritic cells" Cancer Gene Therapy 4:17-25 (1997).

Ace et al, "Construction and characterization of a herpes simplex virus type 1 mutant unable to transinduce immediate-early gene expression" J. Virology 63:2260-2269 (1989).

Smith et al, "Evidence that the herpes simplex virus immediate early protein ICP27 acts post-transcriptionally during infection to regulate gene expression" Virology 186:74-66 (1992).

Rice & Knipe, "Genetic evidence for two distinct transactivation functions of the herpes simplex virus α protein ICP27" J. Virology 64:1704-1715 (1990).

DeLuca et al, "Isolation and characterization of deletion mutants of herpes simplex virus type 1 in the gene encoding immediate-early regulatory protein ICP4" J. Virology 56:558-570 (1985).

McFarlane et al, "Hexamethylene bisacetamide stimulates herpes simplex virus immediate early gene expression in the absence of trans-induction by Vmw65" J. Gen. Virology 73:285-292 (1992).

Lokensgard et al, "Long-term promoter activity during herpes simplex virus latency" J. Virology 68:7148-7158 (1994).

MacLean et al, "Investigation of herpes simplex virus type 1 genes encoding multiply inserted membrane proteins" J. Gen. Virology 72:897-906 (1991).

Gossen & Bujard, "Tight control of gene expression in mammalian cells by tetracycline-responsive promoters" Proc. Natl. Acad. Sci. USA 89:5547-5551 (1992).

Smiley & Duncan, "Truncation of the C-terminal acidic transcriptional activation domain of herpes simplex virus VP16 produces a phenotype similar to that of the in1814 linker insertion mutation" J. Virology 71:6191-6193 (1997).

Girolomoni & Ricciardi-Castagnoli, "Dendritic cells hold promise for immunotherapy" Immunology Today 18(3):102-104 (1997).

Dilloo et al, "A novel herpes vector for the high-efficiency transduction of normal and malignant human hematopoietic cells" Blood 89:119-127 (1997).

Caux et al. "GM-CSF and TNF-α cooperate in the generation of dendritic Langerhans cells" Nature 360:258-261 (1992).

Coffin & Latchman In: Genetic Manipulation of the Nervous System, pp. 99-114 Academic Press, London (1996).

Goldsmith et al. "Infected cell protein (ICP) 47 enhances herpes simplex virus neurovirulence by blocking the $CD8^+T$ cell response" J. Exp. Med. 87:341-348 (1998).

Gough & Murray "Expression of the hepatitis B virus surface, core and E antigen genes by stable rat and mouse cell lines" J. Mol. Biol. 162:43-67 (1982).

Inaba et al. "Identification of proliferating dendritic cell precursors in mouse blood" J. Exp. Med. 175:11057-1167 (1992).

Jones et al. "Mutational analysis of the herpes simplex virus virion host shutoff protein: Evidence that vhs functions in the absence of other viral proteins" J. Virology 69:4863-4871 (1995).

Kruse et al. "Mature dendritic cells infected with herpes simplex virus type 1 exhibit inhibited T-cell stimulatory capacity" J. Virology 74:7127-7136 (2000).

Salio et al. "Inhibition of dendritic cell maturation by herpes simplex virus" Eur. J. Immunol. 20:3245-3253 (1999).

Sallusto & Lazavecchia "Efficient presentation of soluble antigen by cultured human dendritic cells is maintained by granulocyte/macrophage colony-stimulating factor plus interleukin 4 and downregulated by tumor necrosis factor α" J. Exp. Med. 179:1109-118 (1994).

Thomas et al. "Herpes simplex virus latency associated transcript encodes a protein which greatly enhances virus growth, can compensate for deficiencies in immediate-early gene expression, and is likely to function during reactivation from virus latency" J. Virology 73:6618-6625 (1999).

Thompson et al "Herpes simplex virus neurovirulence and productive infection of neural cells is associated with a function which maps between 0.82 and 0832 map units of the HSV genome" Virology 172:435-450 (1998).

Wagstaff et al. "Gene transfer using a disabled herpes virus vector containing the EMCV IRES allows multiple gene expression *in vitro* and *in vivo*" Gene Therapy 5:1566-1570 (1998).

* cited by examiner

HERPES VIRUSES FOR IMMUNE MODULATION

This application is a continuation-in-part of application Ser. No. 09/833,073, filed Apr. 12, 2001, now U.S. Pat. No. 6,713,067; the entire content of which is hereby incorporated by reference in this application. Priority benefit is also claimed of Appln. No. GB 0009079.5, filed Apr. 12, 2000.

FIELD OF THE INVENTION

The present invention relates to attenuated herpes simplex viruses capable of efficiently infecting dendritic cells. It also relates to the use of such viruses in immunotherapy approaches to the treatment of disease.

BACKGROUND TO THE INVENTION

Dendritic cells (DCs) are the most potent antigen presenting cells and are efficient at inducing responses even to antigens to which the immune system has become tolerant. Thus for tumour immunotherapy, in which an immune response is raised against a tumour, the use of DCs may be ideal if they were made to present tumour specific antigens. DCs might also be used to present antigens derived from infectious agents, such as bacteria, viruses or parasites, providing protective or therapeutic vaccines for such diseases. However effective transfer of antigens into DCs for any of these targets has proved the greatest problem with this approach.

To provide a realistic chance of generating a therapeutic immune response against a tumour antigen or other disease related antigen, several conditions have to be met. Firstly, it is necessary to identify molecules whose expression is tumour or disease specific (or at least selective), and which can therefore serve as the target for an immune response. This task has proved very difficult for the majority of common tumours, but is solved in for example the case of cervical cancer by the presence, in most cases, of the viral oncogenes E6 and E7, and for other tumours, good candidate antigens are beginning to be identified. For example the MUC-1 gene product is over expressed in a number of tumours, including 90% of ovarian cancers. Various other tumour associated antigens have also been identified, any of which might be used in an immunotherapy treatment of cancer. These include gp100, MART-1 tyrosinase, MAGE, CEA, PSA and many others. Further tumor associated antigens will no doubt continue to be discovered over time. Secondly, following the identification of the antigen/antigens, it is necessary to deliver the antigens in an immunogenic form to the immune system. To generate the cellular immune response critical for tumour rejection, this means the proteins must either be delivered inside the cytoplasm of a host cell (a difficult task for high molecular weight protein antigens) or synthesized by the host cells themselves after gene delivery or DNA immunisation. Viral vectors which have been considered for this purpose include vaccinia, adenoviruses, or retroviruses.

The cell-type which is now widely recognised as providing the optimal immune stimulus is the dendritic cell (DC; see for example Girolomoni and Ricciardi-Castagnoli, 1997). Indeed the DC appears to be the only cell-type capable of stimulating a primary immune response in vivo, and moreover has even been shown to be capable of breaking established tolerance in certain circumstances. A number of groups are exploring the use of DCs in autologous adoptive immunotherapy protocols to stimulate immune responses against tumours in the hope that they may show a therapeutic effect. Such protocols involve culture and/or enrichment of DCs from peripheral blood, in vitro loading of DCs with antigen and reintroduction of the DCs to the patient or direct in vivo loading of DCs with antigen. However this approach has been hampered by the absence of efficient means by which to load these cells with antigens. Recent work has however shown that presentation of antigens by peptide pulsed DCs has produced anti-tumour responses in vivo (Celluzzi et al., 1996; Zitvogel et al., 1996). As regard to viral vectors, retroviruses do not give high efficiency gene delivery to dendritic cells (Reeves et al., 1996; Aicher et al., 1997), and in our hands, unlike work reported by others (Arthur et al., 1997), adenoviruses only give low efficiency gene delivery.

We have previously tested and reported that herpes simplex viruses (HSV) can efficiently infect and deliver genes to dendritic cells (Coffin et al., 1998; WO 00/08191). HSV has a number of advantages over other vector systems for this purpose, in that it can efficiently infect a wide variety of cell-types (including some very hard to infect with other vector systems e.g. Dilloo et al., 1997; Coffin et al., 1998), is easy to manipulate, and can accept large DNA insertions allowing the expression of multiple genes (reviewed by Coffin and Latchman 1996). Delivery of multiple antigens to dendritic cells ex vivo followed by re-introduction into the body or direct administration of antigens to dendritic cells in vivo may be particularly promising approaches to the treatment of some cancers and infectious diseases.

WO 00/08191 teaches that wild type herpes simplex viruses prevent antigen processing occurring in infected dendritic cells and that herpes viruses that either lack both functional UL43 and vhs genes or contain mutations that minimise immediate early gene expression are capable of efficiently infecting dendritic cells without preventing antigen processing occurring in the infected cells.

SUMMARY OF THE INVENTION

We have found that disruption of the gene encoding the virion host shut-off protein (vhs) in HSV vectors enables efficient dendritic cell activation to occur in HSV infected cells. Disruption of the UL43 gene is not also needed. It has previously been shown that HSV infected dendritic cells usually do not become activated either by infection itself, or by other stimuli (Salio et al 1999, Kruse et al 2000).

We have identified a previously unknown function of the vhs protein in preventing dendritic cell activation. Dendritic cell activation is defined as the up-regulation of certain cell surface markers as compared to the non-activated state. These markers include CD83 and CD86. Dendritic cell activation may be stimulated by treatment with lipopolysaccharide (LPS). LPS treatment of dendritic cells infected with HSV does not result in the up-regulation of CD83 or CD86. We have shown that LPS treatment of dendritic cells infected with a mutant HSV in which vhs is inactivated and which have either a functional or non-functional UL43 gene up-regulates both CD83 and CD86. Up-regulation of CD83 and CD86 is not observed following LPS treatment of dendritic cells infected with viruses comprising a functional vhs gene. Thus our results indicate that, for transduced dendritic cells to maximally stimulate an immune response following herpes virus infection, the gene encoding vhs should be disrupted but the gene encoding UL43 need not be.

We have now identified combinations of mutations to the HSV genome which give enhanced activation and functionality of dendritic cells. These HSV mutants, in addition to the mutation of vhs, have ICP47 and VMW65 and/or ICP22 mutated. These viruses give enhanced activation of dendritic cells as measured by the up-regulation of CD80, CD83, CD86, MHC class I, MHC class II and by mixed leukocyte reactions, particularly in the absence of LPS. Thus, with wild type virus dendritic cells are not activated with or without LPS. With the viruses provided as examples in WO 00/08191, LPS mediated activation of dendritic cells is not blocked and a subset of the markers tested are up-regulated without LPS. The viruses described here give up-regulation of all relevant markers tested in the absence of LPS.

Accordingly, the present invention provides a method of stimulating an immune response in a human or animal subject, which method comprises administering to a subject in need thereof an effective amount of an attenuated herpes virus which:

(i) lacks a functional vhs gene, or a functional equivalent thereof;

(ii) lacks a functional ICP47 gene, or a functional equivalent thereof; and (iii) is incapable of expressing a substantial amount of functional ICP22, or a functional equivalent thereof, in mammalian dendritic cells.

The virus may be incapable of expressing a substantial amount of functional ICP22, or a functional equivalent thereof as a result of a mutation in the VMW65 gene which abolishes its transcriptional-activation activity (e.g. vmw65 mutations as in Ace et al., 1989 or Smiley et al 1997). As an alternative, the virus may lack a functional ICP22 gene.

Preferably said virus is a herpes simplex virus. More preferably, said virus is HSV1 or HSV2. The immune response may be generated by the infection of dendritic cells in vitro and administration of the infected cells to a patient, or by direct administration of the virus in vivo. Thus the viruses described may be directly administered to patients by any route which results in the infection of dendritic cells.

Also provided by the present invention are:

an attenuated herpes virus which:

(i) lacks a functional vhs gene, or a functional equivalent thereof;

(ii) lacks a functional ICP47 gene, or a functional equivalent thereof; and (iii) is incapable of expressing a substantial amount of functional ICP22, or a functional equivalent thereof, in mammalian dendritic cells;

a dendritic cell infected with a virus of the invention;

a pharmaceutical composition comprising an effective amount of a virus of the invention and a pharmaceutically acceptable carrier or diluent; and a method of activating dendritic cells, which method comprises infecting said dendritic cell with an attenuated herpes virus which:

(i) lacks a functional vhs gene, or a functional equivalent thereof;

(ii) lacks a functional ICP47 gene, or a functional equivalent thereof; and (iii) is incapable of expressing a substantial amount of functional ICP22, or a functional equivalent thereof, in mammalian dendritic cells.

DETAILED DESCRIPTION OF THE INVENTION

A. Viruses

A virus of the invention is capable of infecting dendritic cells without preventing the infected dendritic cells from being activated. Preferably dendritic cells infected with a virus of the invention at a multiplicity of infection (MOI) of 1 are activated. Activation may be measured by the up-regulation of surface markers including CD80, CD83, CD86, MHC Class I and MHC Class II.

A virus of the invention does not prevent the activation of dendritic cells. To determine when a virus activates dendritic cells, dendritic cells are infected with the virus at a MOI of 1 or more and surface markers expressed by infected dendritic cells are assessed. Surface marker expression may be monitored by any suitable means such as by FACS analysis. The levels of these markers on the cell surface will be higher, preferably significantly higher in infected as compared to non-infected dendritic cells.

A virus of the invention is an attenuated herpes virus which:

(i) lacks a functional vhs gene, or a functional equivalent thereof;

(ii) lacks a functional ICP47 gene, or a functional equivalent thereof; and (iii) is incapable of expressing substantial levels of functional ICP22, or a functional equivalent thereof, in mammalian dendritic cells.

A virus which is incapable of expressing a substantial amount of functional ICP22, or a functional equivalent thereof, in mammalian dendritic cells which have been infected with the virus expresses substantially no ICP22 in mammalian dendritic cells infected with the virus. Substantially no ICP22 means no ICP22 or an amount of ICP22 which is not detectable or only just detectable. Any suitable means may be used to detect expression of ICP22. Such suitable means will be apparent to those skilled in the art.

The mammalian dendritic cells are preferably human dendritic cells and more preferably dendritic cells of the subject. Expression of ICP22 in dendritic cells of the subject may be easily determined, for example following preparing dendritic cells from a blood sample from the subject.

Expression of functional ICP22 may be prevented by mutating the ICP22 gene of the virus so that the virus is incapable of expressing any functional ICP22. Reduced expression of ICP22 may be effected by other mutations in the virus. For example, a mutation in the VMW65 gene which abolishes its transcriptional-activation activity effectively prevents the expression of functional ICP22 by the virus when introduced into mammalian dendritic cells.

Thus, a virus of the invention capable of activating dendritic cells typically lacks a functional gene encoding vhs, a functional ICP47 gene, a functional VMW65 gene and/or a functional ICP22 gene (in HSV) or homologues or functional equivalents thereof in other viral species.

The virus may contain one or more additional mutation. The additional mutations preferably minimise the toxicity of the virus. Typically such mutations result in reduced or minimised immediate early (IE) gene expression. Prevention or reduction of IE gene expression prevents or reduces virus replication. Such mutations include, for example, inactivating mutations in the genes encoding ICP4, ICP27 and/or ICP0, preferably ICP27 and/or ICP4.

A virus of the invention may or may not comprise a functional UL43 gene.

For direct use in vivo some degree of replication competence may typically be beneficial in boosting the immune responses induced. Thus in these circumstances, a virus of the invention preferably lacks a functional vhs gene and may also lack one or more functional genes which are necessary for fall pathogenicity of the virus but which are not necessary for viral replication. Such genes include those encoding ICP34.5, ICP6, thymidine kinase and glycoproteins such as gH. Preferably, however, the gene encoding thymidine kinase is functional as mutation of this gene would render the virus insensitive to anti-viral agents such as acyclovir.

Although the present invention has been exemplified using herpes simplex viruses, it will be understood that other viruses of the herpesviridae family may be modified to reduce the prevention of dendritic cell activiation of infected dendritic cells. In particular, such viruses may include *varicella zoster* virus, *pseudo-rabies* virus or *bovine herpes* viruses.

When the virus of the invention is a *herpes simplex* virus, the virus may be derived from, for example, HSV1 or HSV2 strains, or derivatives thereof, preferably HSV1. Derivatives include inter-type recombinants containing DNA from HSV1 and HSV2 strains. Such inter-type recombinants are described in the art, for example in Thompson et al (1988) and Meignier et al (1988). Derivatives preferably have at least 70% sequence homology to either the HSV1 or HSV2 genomes, more preferably at least 80%, even more preferably at least 90 or 95%, typically as measured by the methods described herein. More preferably, a derivative has at least 70% sequence identity to either the HSV1 or HSV2 genome, more preferably at least 80% identity, even more preferably at least 90%, 95% or 98% identity.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Derivatives which may be used to obtain the viruses of the present invention include strains that already have mutations in genes which it is desired to functionally inactivate in a virus of the invention, for example vhs inactivated strains (as in Jones et al.1995), ICP47 inactivated strains (as in Goldsmith et al. 1998), strain d120 which has a deletion in ICP4 (DeLuca et al., 1985), strain d27-1 (Rice and Knipe, 1990) which has a deletion in ICP27) or strain d92 which has deletions in both ICP27 and ICP4 (Samaniego et al., 1995). Use of these strains will reduce the number of steps required to produce the mutant HSV strains of the present invention.

The terminology used in describing the various HSV genes is as found in Coffin and Latchman, 1996.

Where functional equivalents of the HSV genes described above exist in other herpes virus species, then these equivalents may be modified. A gene which is functionally equivalent to an HSV gene typically exhibits sequence homology, either amino acid or nucleic acid sequence homology, to the corresponding HSV gene. Typically, a functional equivalent of an HSV gene will be at least 15%, preferably at least 20%, more preferably at least 30%, 40% or 50% identical at the amino acid level to the corresponding HSV gene.

The gene encoding vhs is the UL41 gene in HSV1 and HSV2. In HSV1 strain 17+ (EMBL accession No. HE1CG) the UL41 gene is from nucleotide 91,170 to nucleotide 92,637. In HSV2 strain HG52 (EMBL accession No. z86099) the UL41 gene is from nucleotide 91,800 to nucleotide 93,275. The gene encoding VMW65 is the VP16 gene in HSV1 and HSV2.

Methods of measuring nucleic acid and protein homology are well known in the art. For example the UWGCG Package provides the BESTFIT program which can be used to calculate homology (for example used on its default settings) (Devereux et al. (1984) *Nucleic Acids Research* 12, p 387–395). The PILEUP and BLAST algorithms can be used to calculate homology or line up sequences (typically on their default settings), for example as described in Altschul (1993) J. Mol. Evol. 36:290–300; Altschul et al. (1990) J. Mol. Biol. 215:403–10.

Software for performing BLAST analyses is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff(1992) *Proc. Natl. Acad. Sci. USA* 89: 10915–10919) alignments (B) of 50, expectation (E) of 10, M=5, N=4, and a comparison of both strands.

The BLAST algorithm performs a statistical analysis of the similarity between two sequences, see e.g., Karlin and Altschul (1993) *Proc. Natl. Acad. Sci. USA* 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Functional equivalents of HSV genes can be identified in a number of ways, for example by probing genomic or cDNA libraries made from other viruses with probes comprising all or part of the HSV gene under conditions of medium to high stringency (for example 0.03M sodium chloride and 0.03M sodium citrate at from about 50° C. to about 60° C.). Alternatively, functional equivalents from other species may also be obtained using degenerate PCR which will use primers designed to target sequences within the functional equivalents encoding conserved amino acid sequences. The primers will contain one or more degenerate positions and will be used at stringency conditions lower than those used for cloning sequences with single sequence primers against known sequences (for example 0.03M sodium chloride and 0.03M sodium citrate at about 40° C.). Functional equivalents may be identified by aligning, using any known alignment method, genomic sequences from another herpes virus with genomic sequences of an HSV strain.

A protein encoded by a gene sharing sequence homology with an HSV gene in a herpes virus is a functional equivalent of an HSV protein if it shares one ore more functional characteristics with the HSV protein. For example, a vhs protein plays a role in reducing protein expression levels in an infected cell by reducing the stability of mRNA. Therefore, a functional equivalent of vhs protein preferably plays a role in shutting down host-cell gene expression by reducing the stability of mRNA. More preferably, a functional equivalent of vhs prevents dendritic cell activation in response to stimuli which activate un-infected dendritic cells.

When a *herpes simplex* virus of the invention lacks a particular functional essential gene, for example a functional vmw65 gene the virus may be propagated using a cell line also containing a non-HSV homologue of vmw65 (e.g. *equine herpes* virus gene 12 or BTIF from *bovine herpes* virus).

B. Methods of Mutation

The various viral genes referred to may be rendered functionally inactive by several techniques well known in the art. For example, they may be rendered functionally inactive by deletion(s), substitution(s) or insertion(s), preferably by deletion. A deletion may remove portions of a gene or the entire gene. For example, deletion of only one nucleotide may be made, resulting in a frame shift. However, preferably larger deletions are made, for example from 2, 3 or 5 to 10, 20, 30, 50, 100 or 200 nucleotide substitutions. Preferably at least 25%, more preferably at least 50% of the total coding and non-coding sequence (or alternatively, in absolute terms, at least 10 nucleotides, more preferably at least 100 nucleotides, most preferably, at least 1000 nucleotides) is deleted or substituted. It is particularly preferred to remove the entire gene and some of the flanking sequences. Inserted sequences may include the heterologous genes described below. Mutations may comprise both deletion(s) and insertion(s). For example, an insertion may be made into the site of a deletion. Thus insertion of a heterologous gene into a viral gene may replace part or all of the viral gene. In particular, it is preferred to insert the heterologous gene into vhs, ICP47, ICP22, ICP27 or ICP4. In the case of the VMW65 gene, the entire gene is not deleted since it encodes an essential structural protein, but an inactivating mutation is typically made which abolishes the ability of VMW65 to activate transcriptionally IE genes (e.g. as in Ace et al., 1989 or Smiley et al., 1997).

Mutations may be made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ or GFP, for screening recombinant viruses by, for example, β-galactosidase activity or fluorescence.

C. Heterologous Genes and Promoters

The viruses of the invention may be modified to carry a heterologous gene/genes. The term "heterologous gene" encompasses any gene. Although a heterologous gene is typically a gene not present in the genome of a herpes virus, a herpes gene may be used provided that the coding sequence is not operably linked to the viral control sequences with which it is naturally associated. The heterologous gene may be any allelic variant of a wild-type gene, or it may be a mutant gene. The term "gene" is intended to cover nucleic acid sequences which are capable of being at least transcribed to produce an RNA molecule, which RNA molecule is preferably capable of being translated to produce a polypeptide or to down-regulate gene expression levels by an anti-sense effect. A virus of the invention may optionally include some or all of 5' and/or 3' transcribed but untranslated flanking sequences naturally, or otherwise, associated with the translated coding sequence of a heterologous gene. It may optionally further include the associated transcriptional control sequences normally associated with the transcribed sequences, for example transcriptional stop signals, polyadenylation sites and downstream enhancer elements.

The heterologous gene/genes may be inserted into the viral genome by homologous recombination of HSV strains with, for example, plasmid vectors carrying the heterologous gene/genes flanked by HSV sequences. The heterologous gene/genes may be introduced into a suitable plasmid vector comprising herpes viral sequences using cloning techniques well-known in the art. The heterologous gene/genes may be inserted into the viral genome at any location provided that the virus can still be propagated. It is preferred that the heterologous gene/genes is inserted into a gene resulting in attenuation of the virus. Heterologous genes may be inserted at multiple sites within the virus genome.

The transcribed sequence of the heterologous gene/genes is preferably operably linked to a control sequence permitting expression of the heterologous gene/genes in dendritic cells, preferably mammalian dendritic cells, more preferably human dendritic cells. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene/genes and a signal for termination of transcription. The promoter is selected from promoters which are functional in mammalian, preferably human dendritic cells. The promoter/promoters may be derived from promoter sequences of eukaryotic genes. For example, promoters may be derived from the genome of a cell in which expression of the heterologous gene is to occur, preferably a mammalian dendritic cell or more preferably a human dendritic cell. With respect to eukaryotic promoters, they may be promoters that function in a ubiquitous manner (such as promoters of β-actin, tubulin) or, alternatively, a dendritic cell-specific manner. Viral promoters may also be used, for example the Moloney murine leukaemia virus long terminal repeat (MMLV LTR) promoter or other retroviral promoters, the human or mouse cytomegalovirus (CMV) IE promoters.

Expression cassettes and other suitable constructs comprising the heterologous gene/genes and control sequences can be made using routine cloning techniques known to persons skilled in the art (see, for example, Sambrook et al., 1989, Molecular Cloning—a laboratory manual; Cold Spring Harbor Press).

In addition, any of these promoters may be modified by the addition of further regulatory sequences, for example enhancer sequences (including elements of the HSV LAT region). Chimeric promoters may also be used comprising sequence elements from two or more different promoters described above, for example an MMLV LTR/LAT fusion promoter (Lokensgard et al., 1994) or promoters comprising elements of the LAT region (WO98/30707).

The LAT region is defined as the region within the long terminal repeats of HSV between the unique long region and the 5' terminus of the LAT RNA transcript approximately 8 kb. There are two LAT regions in the HSV genome. For example, in HSV1 strain 17+ (GenBank accession no. HE1CG) one LAT region is the region from the start of the internal long repeat region at nucleotide 117,160 to the polyA site for the LAT RNA transcript of approximately 8 kb at nucleotide 127,142 and the second LAT region is the equivalent region in the terminal long repeat region. In other strains of HSV1 and in strains of HSV2, one LAT region is between nucleotides corresponding to 117,160 and 127,142 and the second LAT region is between the equivalent nucleotides in the terminal long repeat region. For example, in HSV2 strain HG52 (GenBank accession no. NC001798) one LAT region is the region from the start of the internal long repeat region at nucleotide 117,987 to the polyA site for the LAT RNA transcript of approximately 8 kb at nucleotide 127,915 and the second LAT region is the equivalent region in the terminal long repeat region.

A preferred promoter element is the LAT P2 region. The LAT P2 region may consist of nucleotides 118866–120219 of HSV strain 17+ (GenBank HE1CG: from PstI-BstXI sites), the corresponding nucleotides of the other LAT region of HSV1 strain 17+, of a LAT region of another HSV1 strain or of any HSV2 strain. The LAT P2 region may be a fragment of nucleotides 118866–120219 of HSV strain 17+, or of the corresponding nucleotides in the other LAT region of HSV1 strain 17+, any other HSV1 strain or any HSV strain. A LAT P2 region is capable of providing a long-term expression capability to promoters to which they are linked are also preferred promoter elements.

The corresponding nucleotides of LAT regions other than the LAT P2 region consisting of nucleotides 118866–120219 of HSV strain 17+ may easily be determined using known methods of sequence alignment. The ability of a LAT P2 region to confer long-term expression activity may readily be determined by techniques known in the art. For example, an expression construct in which a marker gene is operably linked to a control sequence being tested may be introduced into dendritic cells and expression of the marker gene in the infected cells may be monitored.

Heterologous genes will typically encode polypeptides of therapeutic use. For example, to promote an immune response specifically against a particular tumour, it will be desirable to transfect dendritic cells with a virus of the invention directing expression of a tumour antigen/antigens. A tumour antigen may be specific to a tumour cell, i.e. present in tumour cells but not in non-tumour cells, or it may be present at higher levels in that tumour cell than in a non tumour cell of that type, for example due to up regulation of expression of the antigen. This will be useful in cancer therapy since an infected dendritic cell of the invention can be used to stimulate the host immune system to react to the tumour-specific or tumour-prevalent antigen/antigens resulting in tumour reduction/regression. In particular, it is preferred that the tumour antigen/antigens is expressed on the surface of the tumour cell, for example a cell surface receptor or cell adhesion protein. Examples of tumour antigens include the MUC-1 gene product (Gendler et al., 1990) which is over expressed in a number of tumours including ovarian cancers, human papillomavirus proteins E6 and E7 which are associated with cervical cancer. MART-I, MAGE-I, gp100 and tyrosinase in melanoma, PSA in prostate cancer, CEA in a number of different types of tumour and Her2neu in various cancers including breast cancer.

Heterologous genes may also encode a polypeptide which is capable of modifying an immune response, for example cytokines (such as α-, β- or γ-interferon, interleukins including IL-1, IL-2, tumour necrosis factor, or insulin-like growth factors I or II) or other immunomodulatory proteins including chemokines such as RANTES, SCF and other molecules such as CD80, CD86, CD40 and CD40 ligand.

The heterologous gene may also encode a polypeptide/ polypeptides of pathogenic origin so that, for example, a dendritic cell infected with a virus of the invention can be used to stimulate the host immune system to produce an immune response to a pathogen, either prior to infection or after infection of the host by the pathogen. Viruses for use in vaccines may typically comprise heterologous genes that encode antigenic polypeptide(s). Preferably such polypeptides of pathogenic origin are derived from pathogenic organisms, for example parasites, bacteria or viruses. Examples of such antigenic polypeptides include hepatitis C virus antigens, hepatitis B surface or core antigens, papillomavirus antigens, HIV antigens and malaria antigens. Viruses comprising heterologous genes from pathogenic organisms may be used for either or both therapeutic and prophylactic treatment. The heterologous gene may encode a herpes virus antigen which is operably linked to a control sequence other than the control sequence to which the herpes virus gene is linked in a naturally occuring herpes virus genome.

Therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus multiple heterologous genes can be accommodated within its genome. For example, from 2 to 6 genes may be inserted into the genome.

There are, for example, at least two ways in which this could be achieved. For example, more than one heterologous gene and associated control sequences could be introduced into a particular HSV strain either at a single site or at multiple sites in the virus genome. It would also be possible to use pairs of promoters (the same or different promoters) facing in opposite orientations away from each other, these promoters each driving the expression of a heterologous gene (the same or different heterologous gene) as described above.

Thus, a virus of the invention may comprise more than one heterologous gene or more than one copy of a heterologous gene. Any number of heterologous genes may be introduced into a virus of the invention provided that the virus retains its ability to infect dendritic cells such that the dendritic cells are activated and its ability to express the heterologous gene(s). For example, a virus may contain from 1 to 30 such as 2 to 20 or 3 to 10 heterologous genes. One copy of each heterologous gene may be present or two or more copies of each heterologous gene may be present.

D. Dendritic Cells

Dendritic cells can be isolated/prepared by a number of means, for example they can either be purified directly from peripheral blood, or generated from CD34+ precursor cells for example after mobilisation into peripheral blood by treatment with G-CSF, or directly from bone marrow. From peripheral blood adherent precursors can be treated with a GM-CSF/IL-4 mixture (Inaba et al., 1992), or from bone marrow non-adherent CD34+ cells can be treated with GM-CSF and TNF-α (Caux et al., 1992) DCs can be routinely prepared from the peripheral blood of human volunteers, similarly to the method of Sallusto and Lanzavecchia, 1994, using purified peripheral blood mononeucleocytes (PBMCs) and treating 2 hour adherent cells with GM-CSF and IL-4. These are then depleted of CD19+ B cells and CD3+, CD2+ T cells using magnetic beads (see Coffin et al., 1998). Other methods may also be used for the preparation of dendritic cells.

E. Therapeutic Uses

Viruses of the invention, and dendritic cells infected with viruses of the invention may be used in methods of therapy. In particular, viruses of the invention, and dendritic cells infected with viruses of the invention, which express tumour antigens may be used in methods of treating cancer. Specifically, the, viruses of the invention, and dendritic cells infected with viruses of the invention may be used to inhibit the growth of various tumours in mammals, including humans, such as, for instance, ovarian, cervical and endometrial tumours and carcinomas, for example mammary carcinoma, lung carcinoma, bladder carcinoma and colon carcinoma. Other neoplasms whose growth may be inhibited include sarcomas, for example soft tissue and bone sarcomas, and hematological malignancies such as leukemias. Particular examples of cancers which may be treated using viruses of the invention and/or dendritic cells infected with viruses of the invention which express tumour antigens include melanomas, leukemias, cervical cancers and ovarian cancers. A virus for use in treating cancer typically comprises a heterologous gene encoding a tumour antigen. Administration of such a virus, or dendritic cells infected with such a virus, will typically result in the generation of an immune response to the tumour antigen.

Viruses of the invention, and dendritic cells infected with viruses of the invention, may be used in methods of treating or preventing pathogenic infections, for example parasitic, bacterial or viral infections. A virus for use in treating a pathogenic infection typically comprises a heterologous gene encoding an antigen from the pathogenic organism. Administration of such a virus, or dendritic cells infected with such a virus, will typically result in the generation of an immune response to antigen from the pathogenic organism. Such viral infections include herpes virus infections. Thus, a virus of the invention may be used to induce immune responses to the virus itself, for example in the treatment or vaccination of HSV1 or HSV2 infection. Where a virus is intended for use in the treatment of HSV1 or HSV2, the virus may optionally contain a heterologous gene, which heterologous gene encodes an HSV antigen (which is not under the control of its natural promoter) or an immunomodulatory molecule. The viruses/dendritic cells may be administered prior to infection to stimulate a protective immune response in the host, or after infection to stimulate the host immune system to combat the infection.

The present invention thus provides a method of stimulating an immune response which method consists essentially of administering to a subject in need thereof an effective amount of an attenuated herpes virus which:
(i) lacks a functional vhs gene, or a functional equivalent thereof;
(ii) lacks a functional ICP47 gene, or a functional equivalent thereof; and
(iii) is incapable of expressing a substantial amount of functional ICP22, or a functional equivalent thereof, in mammalian dendritic cells.

Also provided is a method of stimulating an immune response which method consists essentially of administering to a subject in need thereof an effective amount of an attenuated herpes virus which:
(i) lacks a functional vhs gene, or a functional equivalent thereof; and
(ii) lacks a functional ICP47 gene or a functional equivalent thereof.

F. Administration

The herpes viruses of the present invention may thus be used to deliver therapeutic genes to a human or animal in need of treatment. The herpes viruses of the invention may be used to treat for example, malignancies and/or pathogenic infections. Herpes viruses of the invention may be particularly useful as vaccines.

The viruses of the invention may be used in a patient, preferably a human patient, in need of treatment. A patient in need of treatment is an individual suffering from cancer, or a patient with a pathogenic infection. The aim of therapeutic treatment is to improve the condition of a patient. Typically therapeutic treatment using a virus of the invention allieviates the symptoms of the cancer. A method of treatment of cancer according to the invention comprises administering a therapeutically effective amount of a virus of the invention to a patient suffering from cancer such that the virus is present in dendritic cells in the patient. Administration of virus of the invention to an individual suffering from a tumour will typically kill the cells of the tumour thus decreasing the size of the tumour and/or preventing spread of malignant cells from the tumour.

Typically therapeutic treatment of a pathogenic infection using a virus of the invention alleviates the symptoms of the infection and preferably kills the pathogenic organism. A method of treatment of a pathogenic infection according to the invention comprises administering a therapeutically effective amount of a virus of the invention to a patient with a pathogenic infection. Preferably the virus enters dendritic cells in the patient or dendritic cells which have been infected with the virus ex vivo are administered to the patient. Prophylactic treatment using a virus of the invention typically leads to the production of antibodies against a tumour antigen or against an antigen from a pathogenic organism in a patient at risk of cancer or a pathological infection. Typically a patient at risk of cancer may be genetically disposed thereto or may have been exposed to or be at risk of exposure to a carcinogen. Typically a patient at risk of a pathogenic infection may be likely to be exposed to a pathogenic organism.

One method for carrying out therapy involves inserting the therapeutic gene/genes into the genome of the herpes virus of the invention, as described above, and then combining the resultant recombinant virus with a pharmaceutically acceptable carrier or diluent to produce a pharmaceutical composition. A pharmaceutical composition comprising an effective amount of a virus of the invention and a pharmaceutically acceptable carrier or diluent is provided by the invention. The pharmaceutical composition may be a vaccine composition. An effective amount of a virus of the invention is an amount which, when administered to a subject, results in the generation or enhancement of an immune response. Suitable carriers and diluents include isotonic saline solutions, for example phosphate-buffered saline. The composition may be formulated for parenteral, intramuscular, intravenous, intraperitoneal, subcutaneous or transdermal administration. Administration may be by biolistic means. Trans- or intra-dermal administration may be particularly preferred.

Infection of dendritic cells with the virus of the invention may be carried out in vivo by administration of a composition comprising the virus to a patient. The pharmaceutical composition is administered in such a way that the virus containing the therapeutic gene/genes, can infect dendritic cells. The amount of virus administered is in the range of from $10^4$ to $10^{10}$ pfu, preferably from $10^5$ to $10^9$ pfu, more preferably about $10^6$ to $10^8$ pfu. When injected intra-dermally or trans-dermally administered, for example using a needle-free device, typically from 10 µl to 1 ml, preferably from 100 µl to 1 ml of virus in a pharmaceutically acceptable suitable carrier or diluent or in a particulate composition is administered Another method involves isolating/preparing dendritic cells from peripheral blood or bone marrow and infecting the cells with the virus of the invention in vitro. Transduced dendritic cells are then typically administered to the patient by intramuscular, intraperitoneal, subcutaneous or intravenous injection, or by direct injection into the lymph nodes of the patient, preferably by intradermal, subcutaneous, intraperitoneal or direct injection into the lymph nodes. Typically from $10^5$ to $10^9$ transduced dendritic cells, preferably from $10^6$ to $10^8$ cells, more preferably about $10^7$ cells are administered to the patient.

Thus, the present invention provides a method of stimulating an immune response in a subject, which method consists essentially of:

(i) infecting dendritic cells ex vivo with a virus of the invention; and (ii) administering the infected dendritic cells to the subject.

This method may optionally include the additional step of extracting dendritic cells from the subject prior to infection. Dendritic cells may be isolated from peripheral blood or bone marrow.

The routes of administration and dosages described are intended only as a guide since a skilled practitioner will be able to determine readily the optimum route of administration and dosage for any particular patient. The dosage may be determined according to various parameters, especially according to, for example, the age, weight and condition of the patient.

The following Examples illustrate the invention.

EXAMPLES

Materials and Methods

Construction and Growth of Viral Strains

Virus strains are derived from HSV1 strain 17+, the nucleotide sequence of which is deposited in GenBank (Accession No. HE1CG). Viral strains were produced and propagated using BHK C-21 cells (ECACC No. 8501143).

For 17+/vhs-/47-/VP16- viruses, 3 mM hexamethylenebisacetamide (HMBA) was included in the media used for virus growth (McFarlane et al., 1992). The control virus 17+/UL43CMVC, FP has a CMV/GFP/pA cassette inserted at the NsiI site in the UL43 gene of HSV1 strain 17+.

Construction of 17+/vhs-/47-/VP16-

In order to construct the vhs-/47-/VP16- virus a number of plasmids were first constructed:

(i) construction of the pΔ47 plasmid.

Plasmid, p47US, consists of a HindIII/SalI PCR fragment with nucleotides 145570–146980 of the 17+syn genome which consists of the region upstream of the start codon of ICP47 (Forward Primer or SEQ ID NO:1—GCATCGATCT-TGTTCTCCGACGCCATC; Reverse Primer or SEQ ID NO:2—GCMGCTTGCTCCCCCCCGACGAGCAG-GAAG) inserted into the HindIII/SalI site of pBluescript (pBSK SK, Stratagene, USA, GenBank#52325). A second PCR fragment with nucleotides 143675–145290, which consists of the region downstream of the stop codon of ICP47, (Forward Primer or SEQ ID NO:3—TCTA-GAGGGTTCGATTGGCAATGTTGTCTCCCG; Reverse Primer or SEQ ID NO:4—TTAACGATCGAGTCCCGGG-TACGACCATCACCCG) was subcloned into the pGemT Easy vector at the poly-T site (Promega, USA). pGemT vector was used as it facilitated the cloning of blunt-end PCR fragments. An EcoR1 fragment from this vector (pGT47DS) was then inserted into the Spe1 site in p47US in order to produce pΔ47. All PCR reactions were performed using Pfu polymerase from Promega, which is a proof-reading polymerase. Restriction digest analysis of the vector was performed to ensure integrity of the vector. Both PCR fragments were sequenced (DNA Sequencing facility, University of Cambridge) and compared to the published sequence data for HSV type-1 (HE1CG, GenBank accession number X14112).

(ii) Construction of the pΔ47 CMV GFP plasmid.

A BbsI/Nru1 fragment from pCDNA3 CMV GFP, containing the marker gene green fluorescent protein under the control of the HCMV IE promoter and bGH polyA signal, was inserted into the HindIII site in PΔICP47. Restriction digest analysis of the vector was performed to ensure integrity of the vector.

(iii) Construction of the pΔVHS plasmid.

Plasmid PΔVHS US consists of a Kpn1/Xho1 PCR fragment with nucleotides 92637–94300 of the 17+syn genome which consists of the region upstream of the start codon of VHS (Forward Primer or SEQ ID NO:5—AATTCTC-GAGGGTCAATTGTAACTGCGGATCGG; Reverse Primer or SEQ ID NO:6—AATTGGTACCGCAAATCT-TCTGGGGTTTCAG) inserted into the Kpn1/Xho1 site of pBluescript (pBSK SK, Stratagene, USA, GenBank#52325). A second PCR fragment with nucleotides 89500–911168, which consists of the region downstream of the stop codon of VHS, (Forward Primer or SEQ ID NO:7—AATTAC-TAGTCTTTAAGCGCAGCATGTATCG; Reverse Primer or SEQ ID NO:8—AATTTCTAGACCAAACGTCAGAC-GAGCGC) was subcloned into the pGemT Easy vector at the poly-T site (Promega, USA). pGemT vector was used as it facilitated the cloning of blunt-end PCR fragments. An EcoR1 fragment from this vector (pGTVHSDS) was then inserted into the EcoR1 site in pVHS US in order to produce pΔVHS. All PCR reactions were performed using Pfu polymerase from Promega, which is a proof-reading polymerase. Both PCR fragments were sequenced (DNA Sequencing facility, University of Cambridge) and compared to the published sequence data for HSV type-1 (HE1CG, GenBank accession number X14112).

(iv) Construction of the pVHS CMV GFP plasmid.

A Bbs1/Nru1 fragment from pCDNA3 CMV GFP, containing the marker gene green fluorescent protein under the control of the HCMV IE promoter and gGH polyA signal was inserted into the Xho1 site in pΔVHS. Restriction digest analysis of the vector was performed to ensure integrity of the vector.

(v) Construction of the pVP16 Smiley plasmid.

Plasmid, pVP16 US, consists of a Xho1/EcoR1 PCR fragment with nucleotides 103790–105590 of the 17+syn genome. This fragment consists of a 1.8 kb 5' region of VP16 which contains the N-terminal structural domain inserted into the Xho1/EcoR1 site of pBluescript (pBSK SK, Stratagene, USA, GenBank#52325). (Forward Primer or SEQ ID NO:9—GCGGCGTCGCGCCCCACCGAG; Reverse Primer or SEQ ID NO:10—GGGGAATTCTAC-CTAGCTAGCAGCTCGTCCCCAGGCTGA-CATCGGTCG). The reverse primer encodes three stop codons, one for each reading frame. A second PCR fragment with nucleotides 102262–103778, which consists of the 3' region of VP16 containing the C-terminal function domain (Forward Primer or SEQ ID NO:11—GAGGACGTGGC-GATGGCGCATG; Reverse Primer or SEQ ID NO:12—TAGGATCCGCTCATCGCCTGGGCGG) was subcloned into the pGemT Easy vector at the poly-T site (Promega, USA). pGemT vector was used as it facilitated the cloning of blunt-end PCR fragments. A BamH1/Sph1 fragment from this vector (pGT VP16 DS) was then inserted into the Not1 site in pVP16 US in order to produce pVP16 Smiley. All PCR reactions were performed using Pfu polymerase from Promega, which is a proof-reading polymerase. Restriction digest analysis of the vector was performed to ensure integrity of the vector. Both PCR fragments were sequenced (DNA Sequencing facility, University of Cambridge) and compared to the published sequence data for HSV type-1 (HE1CG, GenBank accession Number X14112).

(vi) Construction of the pVP16 Smiley IRES GFP plasmid.

A EcoR1/Srf1 fragment from pR19 IRES GFP, containing the marker gene green fluorescent protein downstream of the EMCV IRES sequence and upstream of the bGG polyA signal, was inserted into the EcoR1/BamH1 sites in pVP16 Smiley. Restriction digest analysis of the vector was performed to ensure integrity of the vector. The construct was stored at −20° C. as plasmid DNA and at −80° C. as a glycerol stock transformed into XL1-Blue cells.

Following construction of the above plasmids the virus was constructed by sequential homologous recombination of the plasmids with HSV1 strain 17+genomic DNA and selection and purification of GFP expressing and non-GFP expressing plaques as appropriate. Thus plasmid (ii) above was recombined with HSV1 strain 17+genomic DNA and GFP expressing plaques selected. The GFP was then removed from this virus by homologous recombination with plasmid (i) to give a virus deleted for ICP47. The resulting virus was then recombined with plasmid (iv) inserting GFP into the vhs locus and this virus recombined with plasmid (iii) to remove the GFP, giving a virus deleted for both vhs and ICP47. The vhs-/ICP47- virus was then recombined with plasmid (v,i) inserting GFP to replace the transactivating region of VP16. GFP was then removed using plasmid (v) to generate the vhs-/ICP47-/VP16- virus.

Dendritic Cell Preparation

DC were prepared from peripheral blood as previously described (Coffin et al 1998). Briefly, peripheral blood mononuclear cells (PBMCs) were prepared from 60 ml of healthy/hepatitis B vaccinated donor blood using lymphoprep (Nycomed). After removal of red cells, non-adherent cells (mainly T cells and B cells) were removed, washed in HBSS and centrifuged at 1400 rpm, 5 minutes, RT. The cell pellet was resuspended in a 2 ml 90% FCS:10% dimethylsulphoxide (DMSO) mix, aliquoted and stored at −80 C for subsequent T cell isolation. Adherent cells were cultured in RPMI medium supplemented with GM-CSF (0.1 µg/ml) and IL-4 (0.05 µg/ml) and incubated for 7 days, at 37 C, 5% $CO_2$. After further lymphoprep purification cells were then magnetically depleted using anti-CD19, anti-CD2 (Harlan) and anti-CD3 (Harlan) antibodies and DC were resuspended in complete RPMI medium for immediate use.

Infection of DC

DC were pelleted at 1400 rpm for 5 minutes at room temperature. DC were then infected at MOI of 1 by resuspension in RPMI medium containing virus for 1 hour at 37 C, 5% $CO_2$, 1 ml of RPMI supplemented with GM-CSF (0.1 µg/ml) and IL-4 (0.05 µg/ml) was then added and DC incubated at 37 C, 5% $CO_2$. For LPS stimulation, RPMI additionally containing 100 ng/ml LPS was used.

Example 1

Viruses of the Invention Activate Dendritic Cells as Measured by Up-regulation of CD80, CD83, CD86, MHC class I and MUC class II Here $1 \times 10^5$ dendritic cells were mock infected, mock infected and activated with LPS or infected with the ICP47-/vhs-/VP16- virus or 17+/UL43CMVGFP at an MOI of 1 by gentle pelleting, resuspension in about 100 µl virus suspension in DMEM, incubation at 37° C. for 1 hour, and transfer into 24 well plates with 2 ml of RPMI/10% FCS+10 ng/ml GM-CSF, 50 ng/ml IL-4. The plates were then incubated at 37° C./5% $CO_2$ overnight. Dendritic cells were also treated with lipopolysaccharide (LPS) a known dendritic cell activator, and untreated as a controls.

Fluorescence activated cell sorting (FACS) was used to detect levels of expression of surface markers (CD80, CD83, CD86, MHC class I, MHC class II) on the treated dendritic cells.

Results

FACS analysis demonstrates that levels of CD80, CD83, CD86, MHC class I and MHC class II are increased as compared to either mock infected cells or cells infected with the control, essentially wild type, virus 17+/UL43CMVGFP virus when infected with the vhs-/ICP47-/VP16- virus indicating activation of the dendritic cells by the vhs/ICP47-IVP16—virus which does not occur following infection with the control virus. Treatment of the cells with LPS, a known activator of DC, has similar effects on surface marker up-regulation as does infection with the vhs-/ICP47-/VP16- virus.

Conclusion

Viruses of the invention unlike previously report strains of HSV, activate dendritic cells as measured by surface marker up-regulation.

REFERENCES

Gendler, S. J. et al.,(1990), J. Biol. Chem. 265:15286–15293.
Aicher, A. et al., (1997), Exp. Hematol. 25:39–44.
Samaniego, L. A. et al., (1995), J. Virol. 69:5705–5715.
Zitvogel, L. et al., (1996), J. Exp. Med 183:87–97.
Celluzzi, C. M. et al., (1996), J. Exp. Med. 183:283–287.
Reeves, M. E. et al., (1996), Cancer Research 56:5672–5677.
Arthur, J. F. et al., (1997), Cancer Gene Therapy 4:17–25.
Coffin, R. S. et al., (1998), Gene Therapy 5:718–722.
Coffin, R. S. and Latchman, D. S. (1996), Genetic Manipulation of the Nervous System (D. S. Latchman Ed.) pp 99–114: Academic Press, London.
Inaba, K. et al., (1992) J. Exp. Med. 175;1157–1167.
Caux, C. et al., (1992), Nature 360:258–261.

Sallusto, F. and Lanzavecchia, A. (1994), J. Exp. Med. 179:1109–1118.
Coffin, R. S. et al., (1996), Gene Therapy 3:886–891.
Ace, C. I. et al., (1989), J. Virol. 63:2260–2269.
Rice, S. A. and Knipe, D. M. (1990), J. Virol. 64:1704–1715.
DeLuca, N. A. et al., (1985), J. Virol. 56: 558–570.
Lokensgard, J. R. et al., (1994), J. Virol. 68:7148–7158.
Smiley, J. R. and Duncan, J. (1997), J. Virol. 71:6191–6193.
Dilloo, D et al. 1997 Blood 89:119–127:
Jones, F. E. et al. 1995 J. Virol 69: 4863–4871
Goldsmith, K et al. 1998 J. Exp Med. 87; 341–348
Salio et al. 1999 Eur. J. Immunol. 29: 3245–3253
Kruse et al 2000 J. Virol. 74, 7127–7136

The invention claimed is:

1. A method of stimulating an immune response in a human or animal subject, which method comprises administering to a subject in need thereof an effective amount of an attenuated herpes virus which:
 (i) lacks a functional vhs gene, or a functional equivalent thereof;
 (ii) lacks a functional ICP47 gene, or a functional equivalent thereof;
 (iii) is incapable of expressing a substantial amount of functional ICP22, or a functional equivalent thereof, in mammalian dendritic cells; and
 (iv) comprises a functional UL43 gene
such that dendritic cells are infected with said virus.

2. The method of claim 1, wherein said virus lacks a functional ICP22 gene or a functional equivalent thereof.

3. The method of claim 1, wherein said virus lacks a functional VMW65 gene, or a functional equivalent thereof, due to a mutation in said gene which abolishes its transcriptional-activation activity.

4. The method of claim 1, wherein said virus is a herpes simplex virus 1 or 2.

5. The method of claim 1, wherein said virus comprises a heterologous gene.

6. The method of claim 5, wherein said heterologous gene is operably linked to a control sequence permitting expression of said heterologous gene in a dendritic cell.

7. The method of claim 6, wherein said heterologous gene encodes a polypeptide of therapeutic use.

8. The method of claim 7, wherein said heterologous gene encodes a polypeptide selected from: a polypeptide, the level of expression of which is increased in or on the surface of tumor cells as compared to non-tumor cells; a polypeptide which is present in or on the surface of tumor cells but absent from non-tumor cells; a polypeptide capable of modifying immune responses; and a polypeptide of parasitic, viral or bacterial origin.

9. The method of claim 5, wherein said virus comprises more than one heterologous gene.

10. The method of claim 5, wherein said virus comprises a heterologous gene or genes capable of modulating an immune response.

11. The method of claim 10, wherein said heterologous gene encodes a chemokine, cytokine or co-stimulatory molecule.

12. The method of claim 1, wherein dendritic cells are infected in vivo following administration of the virus to the subject.

13. The method of claim 12, wherein the virus is administered by injection, by infusion, by an intra- or trans-dermal route or by biolistic means.

14. The method of claim 1, wherein the virus is administered to the subject by the steps of:
 (i) infecting dendritic cells with said virus ex vivo;
 (ii) administering the infected dendritic cells to said subject.

15. The method of claim 14 further comprising isolating or preparing dendritic cells from peripheral blood or bone marrow prior to infection.

16. The method of claim 14, wherein the dendritic cells are administered by injection, by infusion, by an intra- or trans-dermal route or by biolistic means.

17. The method of claim 14, wherein said dendritic cells are human dendritic cells.

18. The method of claim 1, wherein the subject is in need of treatment or protection against a pathogenic infection.

19. The method of claim 1, wherein the subject is in need of treatment or protection against cancer.

20. An isolated dendritic cell infected with an attenuated herpes virus which:
 (i) lacks a functional vhs gene, or a functional equivalent thereof;
 (ii) lacks a functional ICP47 gene, or a functional equivalent thereof;
 (iii) is incapable of expressing a substantial amount of functional ICP22, or a functional equivalent thereof, in mammalian dendritic cells; and
 (iv) comprises a functional UL43 gene.

21. A method of activating dendritic cells, which method comprises infecting dendritic cells with an attenuated herpes virus which:
 (i) lacks a functional vhs gene, or a functional equivalent thereof;
 (ii) lacks a functional ICP47 gene, or a functional equivalent thereof;
 (iii) is incapable of expressing a substantial amount of functional ICP22, or a functional equivalent thereof, in mammalian dendritic cells; and
 (iv) comprises a functional UL43 gene.

22. The method of claim 21, wherein said virus lacks a functional ICP22 gene, or a functional equivalent thereof.

23. The method of claim 22, wherein said virus further lacks a functional ICP34.5 gene, or a functional equivalent thereof.

24. The method of claim 21, wherein said virus lacks a functional VMW65 gene, or a functional equivalent thereof, due to a mutation in said gene which abolishes its transcriptional-activation activity.

25. The method of claim 21, wherein said virus comprises a heterologous gene.

26. The method of claim 25, wherein said heterologous gene is operably linked to a control sequence permitting expression of said heterologous gene in a dendritic cell.

27. The method of claim 25, wherein said heterologous gene encodes a polypeptide of therapeutic use.

28. The method of claim 25, wherein said heterologous gene encodes a polypeptide selected from: a polypeptide, the level of expression of which is increased in or on the surface of tumor cells as compared to non-tumor cells; a polypeptide which is present in or on the surface of tumor cells but absent from non-tumor cells; a polypeptide capable of modifying immune responses; and a polypeptide of parasitic, viral or bacterial origin.

29. The isolated dendritic cell of claim 20, wherein said virus lacks a functional ICP22 gene, or a functional equivalent thereof.

30. The isolated dendritic cell of claim 29, wherein said virus further lacks a functional ICP34.5 gene, or a functional equivalent thereof.

31. The isolated dendritic cell of claim 20, wherein said virus lacks a functional VMW65 gene, or a functional equivalent thereof, due to a mutation in said gene which abolishes its transcriptional-activation activity.

32. The isolated dendritic cell of claim 20, wherein said virus comprises a heterologous gene.

33. The isolated dendritic cell of claim 32, wherein said heterologous gene is operably linked to a control sequence permitting expression of said heterologous gene in a dendritic cell.

34. The isolated dendritic cell of claim 32, wherein said heterologous gene encodes a polypeptide of therapeutic use.

35. The isolated dendritic cell of claim 32, wherein said heterologous gene encodes a polypeptide selected from: a polypeptide, the level of expression of which is increased in or on the surface of tumor cells as compared to non-tumor cells; a polypeptide which is present in or on the surface of tumor cells but absent from non-tumor cells; a polypeptide capable of modifying immune responses; and a polypeptide of parasitic, viral or bacterial origin.

36. The method of claim 2, wherein said virus further lacks a functional ICP34.5 gene or a functional equivalent thereof.

* * * * *

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1
gcatcgatct tgttctccga cgccatc                                           27

<210> SEQ ID NO 2
<211> LENGTH: 31
<212> TYPE: DNA
<213> ORGANISM: Artificial Sequence
<220> FEATURE:
<223> OTHER INFORMATION: primer

<400> SEQUENCE: 2
gcaagcttgc tcccccccga cgagcaggaa g                                      31

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
tctagagggt tcgattggca atgttgtctc ccg                                    33

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
ttaacgatcg agtcccgggt acgaccatca cccg                                   34

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
aattctcgag ggtcaattgt aactgcggat cgg                                    33

<210> SEQ ID NO 6
<211> LENGTH: 31
<212> TYPE: DNA
<213> ORGANISM: Artificial Sequence
```

```
<220> FEATURE:
<223> OTHER INFORMATION: primer

<400> SEQUENCE: 6
aattggtacc gcaaatcttc tggggtttca g                              31

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
aattactagt ctttaagcgc agcatgtatc g                              31

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
aatttctaga ccaaacgtca gacgagcgc                                 29

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gcggcgtcgc gccccaccga g                                         21

<210> SEQ ID NO 10
<211> LENGTH: 49
<212> TYPE: DNA
<213> ORGANISM: Artificial Sequence
<220> FEATURE:
<223> OTHER INFORMATION: primer

<400> SEQUENCE: 10
ggggaattct acctagctag cagctcgtcc cccaggctga catcggtcg            49

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gaggacgtgg cgatggcgca tg                                        22

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
taggatccgc tcatcgcctg ggcgg                                     25
```